(12) United States Patent
Ambring

(10) Patent No.: US 10,226,383 B2
(45) Date of Patent: Mar. 12, 2019

(54) WELDING HELMET WITH REMOVABLE NECK GUARD

(71) Applicant: ESAB AB, Gothenburg (SE)

(72) Inventor: Josefin Ambring, Gothenburg (SE)

(73) Assignee: ESAB AB, Gotenborg (SE)

( * ) Notice: Subject to any disclaimer, the term of this patent is extended or adjusted under 35 U.S.C. 154(b) by 0 days.

(21) Appl. No.: 15/298,969

(22) Filed: Oct. 20, 2016

(65) Prior Publication Data

US 2018/0110656 A1 Apr. 26, 2018

(51) Int. Cl.
| | |
|---|---|
| *A61F 9/06* | (2006.01) |
| *A42B 3/10* | (2006.01) |
| *A41D 13/05* | (2006.01) |
| *A41D 13/08* | (2006.01) |

(52) U.S. Cl.
CPC ............ *A61F 9/06* (2013.01); *A41D 13/0512* (2013.01); *A41D 13/0518* (2013.01); *A41D 13/08* (2013.01); *A42B 3/105* (2013.01)

(58) Field of Classification Search
CPC ... A61F 9/06; A41D 13/0512; A41D 13/0518; A42B 3/105
See application file for complete search history.

(56) References Cited

U.S. PATENT DOCUMENTS

| | | | |
|---|---|---|---|
| 1,874,872 A | 8/1932 | Bowers | |
| 2,016,775 A | 10/1935 | Gingg | |
| 2,469,810 A * | 5/1949 | Bowers | A61F 9/06 |
| | | | 2/8.1 |
| 2,725,559 A * | 12/1955 | Wagner | A61F 9/06 |
| | | | 2/8.1 |
| 2,926,357 A * | 3/1960 | Edwards | A42B 3/225 |
| | | | 2/8.1 |
| 3,026,525 A * | 3/1962 | Gyorfy | A42B 3/225 |
| | | | 2/202 |
| 3,369,255 A * | 2/1968 | Bolle | A61F 9/025 |
| | | | 2/427 |
| 3,609,763 A * | 10/1971 | Raney | A42B 3/105 |
| | | | 2/415 |

(Continued)

FOREIGN PATENT DOCUMENTS

| | | | |
|---|---|---|---|
| CN | 2098909 U | 3/1992 | |
| CN | 106859847 A | 6/2017 | |
| GB | 1526574 A * | 9/1978 | ............. A42B 3/105 |

OTHER PUBLICATIONS

3M Speedglas 9100 Welding Helmet, Optimum Comfort and Protection Brochure, St. Paul, MN, 3M 2008.

(Continued)

*Primary Examiner* — Andrew W Sutton
(74) *Attorney, Agent, or Firm* — Edell, Shapiro & Finnan, LLC

(57) ABSTRACT

A welding helmet includes a helmet shell contoured to substantially cover a user's face, and a neck guard removably attachable to a bottom portion of the helmet shell. The neck guard has a predetermined contour, aligning with a portion of the helmet shell contour, and is configured to cover at least a portion of a user's neck when the welding helmet is fitted to the head of the user. The neck guard is removably attachable to the helmet shell by a mechanical fastening arrangement, which can include a plurality of fasteners.

20 Claims, 7 Drawing Sheets

(56) References Cited

U.S. PATENT DOCUMENTS

| | | | | |
|---|---|---|---|---|
| 3,668,705 | A * | 6/1972 | Garbisch | A42B 3/003 2/10 |
| 3,825,952 | A * | 7/1974 | Pershing | A42B 3/0473 2/205 |
| 4,017,906 | A * | 4/1977 | Bochynsky | A42B 3/0473 2/10 |
| 4,042,976 | A * | 8/1977 | Reynolds | A41D 23/00 2/135 |
| 5,329,641 | A * | 7/1994 | Kalhous | A42B 3/105 2/422 |
| 6,185,739 | B1 | 2/2001 | Verkic et al. | |
| 6,289,521 | B1 * | 9/2001 | Ikeda | A42B 3/326 2/421 |
| 6,874,170 | B1 * | 4/2005 | Aaron | A41D 13/0512 2/421 |
| 7,093,302 | B1 * | 8/2006 | Burns | A61F 9/06 2/8.1 |
| 2010/0107318 | A1 * | 5/2010 | Asta | A42B 3/105 2/424 |
| 2011/0030114 | A1 | 2/2011 | Merikoski et al. | |
| 2011/0259186 | A1 * | 10/2011 | Rensink | F41H 1/02 89/36.02 |
| 2012/0216340 | A1 * | 8/2012 | Asta | A42B 3/105 2/422 |
| 2014/0298557 | A1 * | 10/2014 | Townsend, Jr. | A61F 9/06 2/8.2 |
| 2015/0196081 | A1 * | 7/2015 | Handfield | A42B 3/105 2/9 |
| 2016/0058080 | A1 * | 3/2016 | Pearce | A41D 13/1184 128/206.12 |
| 2017/0065016 | A1 * | 3/2017 | Chuback | A42B 3/0473 |

OTHER PUBLICATIONS

International Search Report and Written Opinion from PCT/IB2017/056447 dated Jan. 15, 2018.

* cited by examiner

WELDING HELMET WITH REMOVABLE NECK GUARD

FIELD OF THE DISCLOSURE

The disclosure generally relates to welding helmet, and more particularly to a welding helmet having a removable neck guard.

BACKGROUND OF THE DISCLOSURE

Welding helmets provide protection for a user during a welding operation by typically protecting a user's face, including his eyes, nose, and mouth, from weld spatter and/or debris. Welding helmets, typically formed of a rigid heat resistant material, may additionally provide protection for the user's chin and neck; however, this coverage is integral to the entire helmet. This is disadvantageous because it provides limited flexibility for a user to be able to rotate their head while wearing the welding helmet without interference between the bottom of the helmet and the user's neck or chest. Additionally, the chin and neck protection arrangements of current welding helmets are not exchangeable or customizable based on a welding operation to be performed by the user. Thus, if a user desires a different chin and neck protection, the user must switch to a different welding helmet entirely.

It is with respect to these and other considerations that the present improvements may be useful.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

In an embodiment according to the present disclosure, a welding helmet comprises a helmet shell contoured to substantially cover a user's face, and a neck guard removably attachable to a bottom portion of the helmet shell. The neck guard has a predetermined contour aligning with a portion of the helmet shell contour, and is configured to cover at least a portion of a user's neck when the welding helmet is fitted to the head of the user.

In an embodiment according to the present disclosure, a welding helmet kit comprises a helmet shell contoured to substantially cover a user's face, a flexible neck guard removably attachable to a bottom portion of the helmet shell, and a rigid neck guard removably attachable to a bottom portion of the helmet shell. The flexible neck guard and the rigid neck guard have a predetermined contour aligning with the helmet shell contour, and are configured to cover at least a portion of a user's neck when the welding helmet is fitted to the head of a user.

BRIEF DESCRIPTION OF THE DRAWINGS

By way of example, a specific embodiment of the disclosed device will now be described, with reference to the accompanying drawings, in which.

DETAILED DESCRIPTION OF THE DRAWINGS

Figure 1:
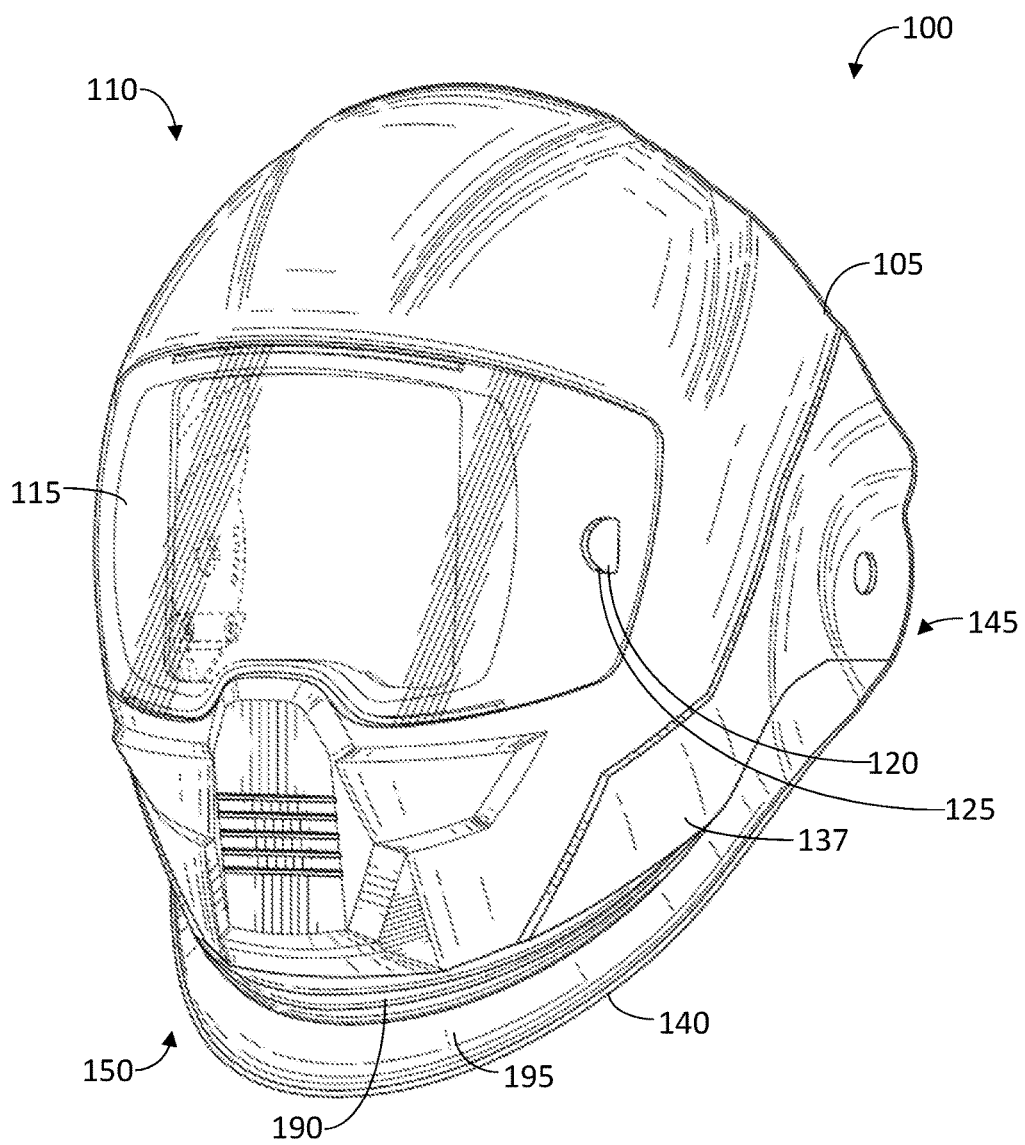
FIG. 1 is a front perspective view illustrating an embodiment of a welding helmet and removable neck guard in accordance with the present disclosure.

The present embodiments will now be described more fully hereinafter with reference to the accompanying drawings, in which several exemplary embodiments are shown. The subject matter of the present disclosure, however, may be embodied in many different forms and should not be construed as limited to the embodiments set forth herein. Rather, these embodiments are provided so that this disclosure will be thorough and complete, and willfully convey the scope of the subject matter to those skilled in the art. In the drawings, like numbers refer to like elements throughout.

Referring to FIG. 1, an embodiment of a welding helmet 100 in accordance with the present disclosure is shown. The helmet 100 may include a helmet shell 105 having a contour 110, which may generally conform to the outline of portions of a user's head and face. For example, the helmet shell contour 110 may be curved around features of the user's face. When the welding helmet 100 is fitted to a user's head, the helmet shell 105 may substantially cover the user's face, including but not limited to the user's eyes, nose, and mouth, to protect the user's face from weld spatter, arc light, debris, and/or fumes during the welding operation.

The helmet shell 105 may be made of a heat resistant plastic material. In an embodiment, the helmet shell 105 may be made of a rigid plastic material to protect the user's face from weld spatter and debris. The helmet shell 105 may be attachable to a head gear assembly (not shown) that is adjustable to fit the helmet 100 to a user's head, so that the helmet shell 105 is positionable over the user's face.

Figure 6:
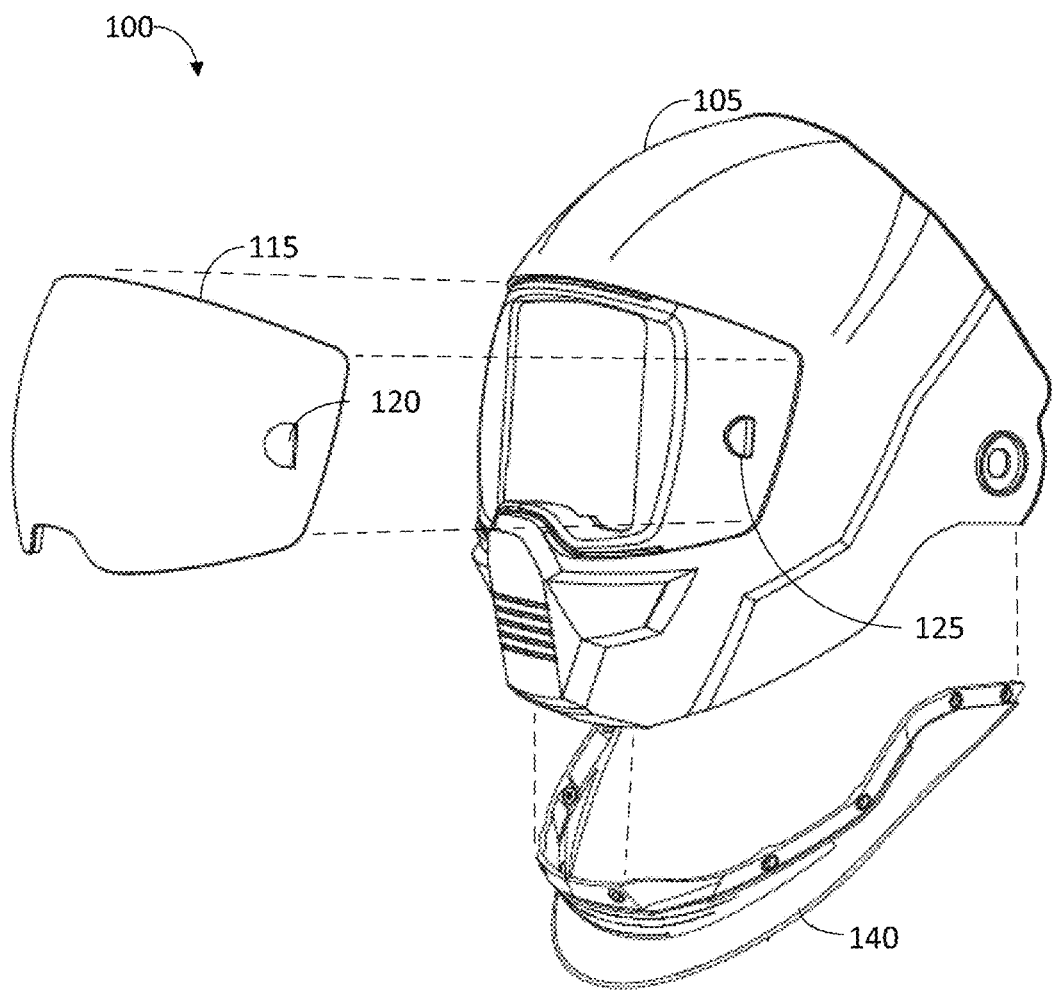
FIG. 6 is an exploded perspective view illustrating an embodiment of the welding helmet of FIG. 1 in accordance with the present disclosure.

The helmet shell 105 may include a viewing area 115, so that the user may see out of the helmet shell 105 when the welding helmet 100 is fitted to the user's head. The viewing area 115 may be made of a clear, transparent, translucent, and/or tinted heat resistant plastic material. As more clearly shown in FIG. 6, the viewing area 115 may include a viewing area connector 120, to connect to a helmet shell connector 125, so that the viewing area 115 is removably coupleable to the helmet shell 105. In an embodiment, the viewing area connector 120 may be an aperture to receive the helmet shell connector 125, which may be a protrusion, although it should be understood that the viewing area connector 120 may be a protrusion and the helmet shell connector 125 may be an aperture for receiving the viewing area connector 120.

Figure 2:
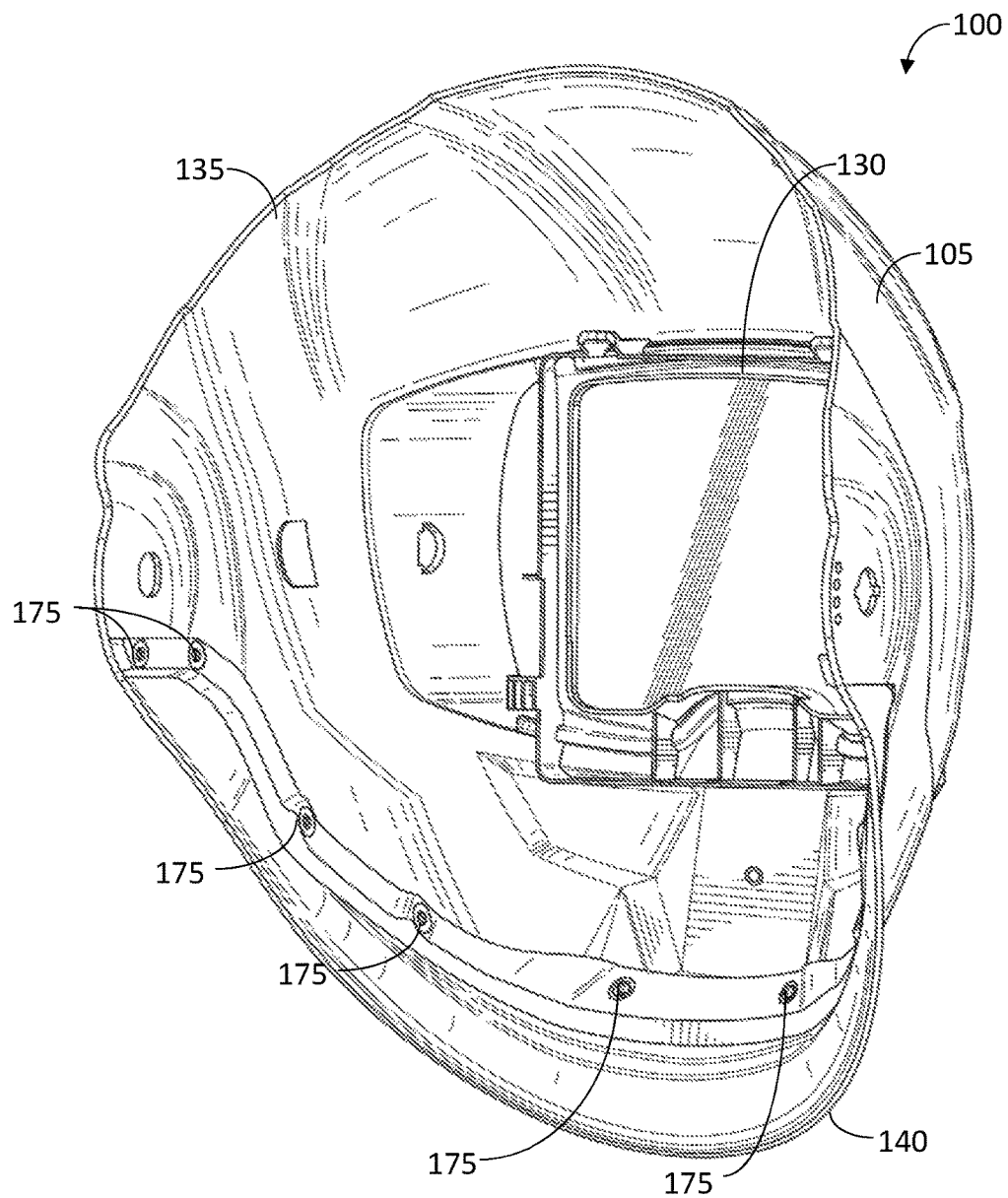
FIG. 2 is a rear perspective view illustrating an embodiment of the welding helmet and removable neck guard shown in FIG. 1.
Figure 4:
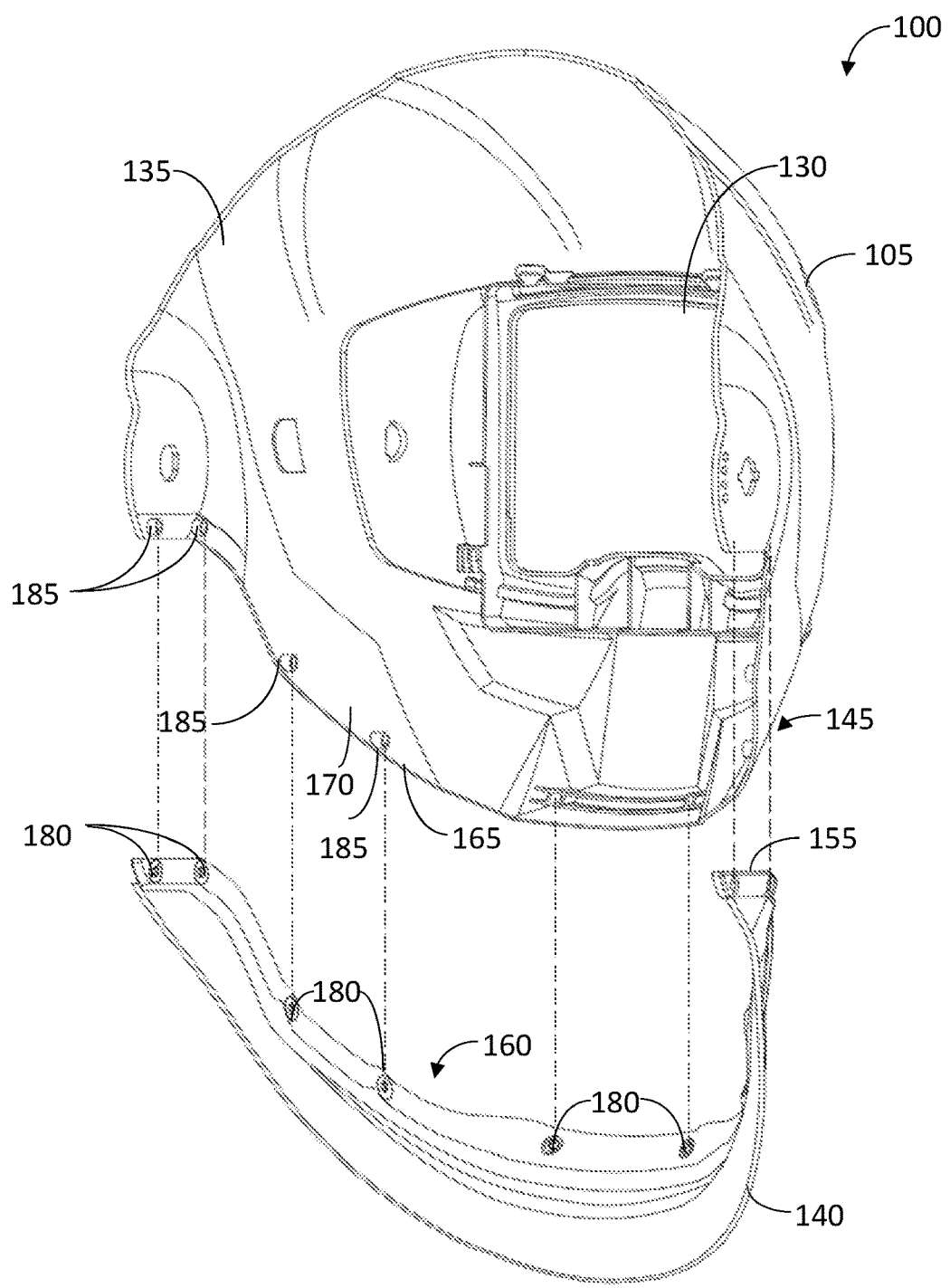
FIG. 4 is a rear perspective view illustrating an embodiment of the welding helmet of FIG. 1, with the neck guard in a detached configuration.

In some embodiments, an auto-darkening filter 130 may be disposed on an interior surface 135 of the helmet shell 105, as shown in FIGS. 2 and 4. The auto-darkening filter 130 may be positioned relative to the viewing area 115 so that the user sees through the auto-darkening screen 130 and the viewing area 115 when the welding helmet 100 is fitted to the head of the user. The auto-darkening filter 130 may protect the user's eyes in some welding operations by reducing the amount of light transmitted to a user's eyes during a welding operation or other operation in which unsafe light levels could otherwise harm the user. The auto-darkening filter 130 may be connected to the interior surface 135 by known attachment mechanisms, including but not limited to fasteners, clamps, snaps, slides, adhesives, and the like.

In some embodiments, the welding helmet 100 may include a neck guard 140. The neck guard 140 may be removably attachable to a bottom portion 145 of the helmet shell 105, so that the neck guard 140 covers at least a portion of a user's neck when the welding helmet 100 is fitted to the head of the user. The neck guard 140 may have a predetermined contour 150, which aligns with a contour of the portion of the helmet shell to which the neck guard attaches. For example, the predetermined neck guard contour 150 may be curved to fit around at least a portion of the user's neck, protecting the user's chin and at least a portion of the neck from weld spatter and debris during a welding operation.

Figure 5:
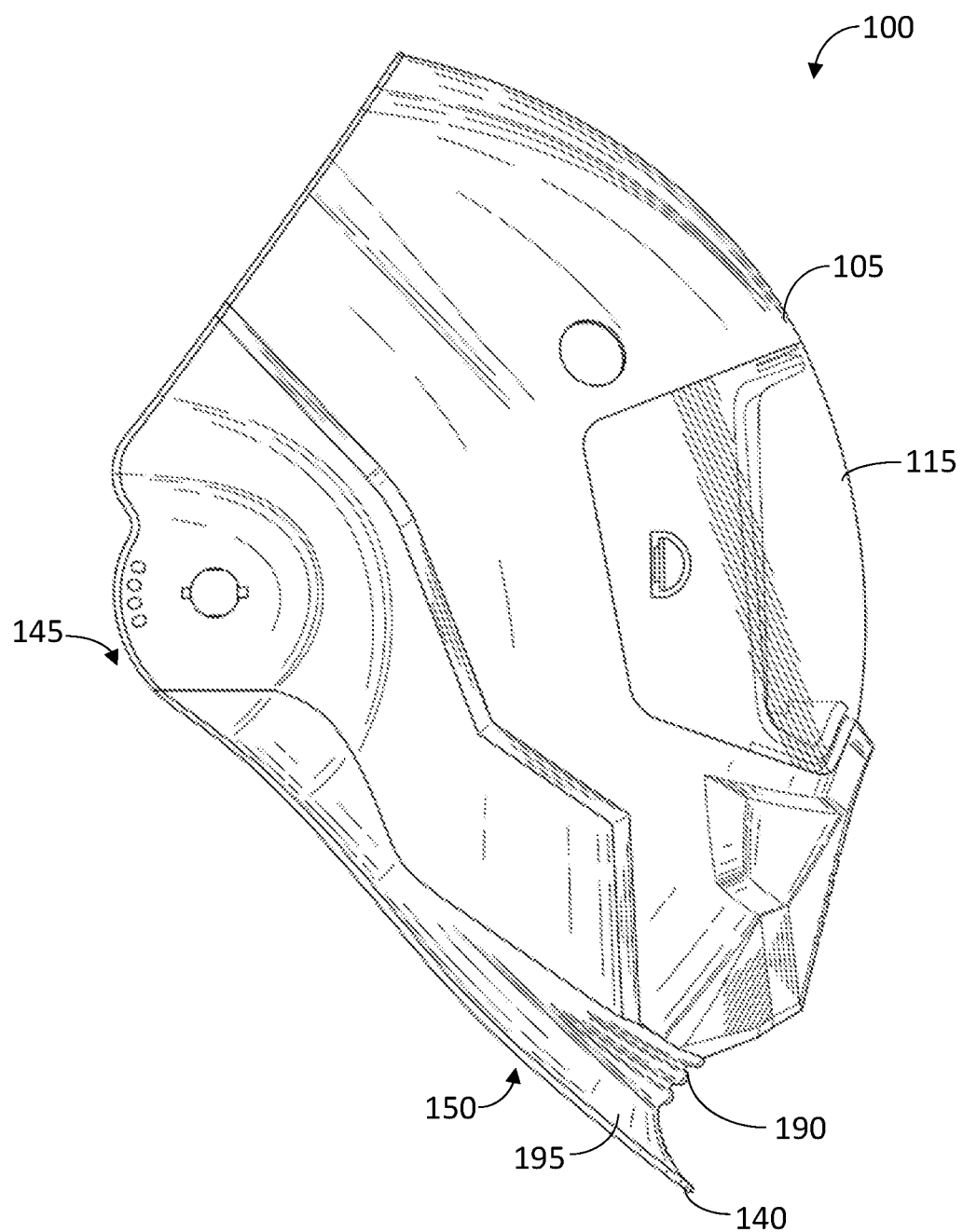
FIG. 5 is a side view illustrating an embodiment of the welding helmet and the removable neck guard as shown in FIG. 1.

In an embodiment, the neck guard 140 may include a bellows portion 190. The bellows portion 190 may be accordion-shaped to provide a degree of flexibility to the neck guard 140, thus enabling the neck guard to compress and expand in response to user movement. As more clearly shown in FIGS. 1, 3, and 5, the bellows portion 190 may include individual bellows elements that extend in a direction generally parallel to the predetermined neck guard contour 150. As will be appreciated, this arrangement of the bellows portion 190 may enable the neck guard to compress when the user bends their neck forward and down, and may enable the neck guard to expand again when the user returns their head to a neutral upright position. The bellows portion 190 may permit additional flexibility in the neck guard 140 for the user to rotate, tilt, and/or move his head and/or neck when the welding helmet 100 is fitted to the user's head.

The neck guard 140 may further include a protective portion 195. The protective portion 195 may be disposed below the bellows portion 190 and may serve as a protective covering for at least a portion of the user's body that is not strictly covered by the helmet shell 105. Primarily the protective portion 195 will provide protection to the user's neck, and in some instances, the user's chest. In the illustrated embodiment the protective portion 195 extends from the bellows portion 190 and follows the predetermined neck guard contour 140.

The neck guard 140, including the bellows portion 190 and the protective portion 195, may be made of a same material as the helmet shell 105, e.g., a heat resistant plastic material. In an embodiment, the neck guard 140 may be made of a rigid plastic material. In other embodiments, the neck guard 140 may be made of a different heat resistant material from the helmet shell 105. For example, the neck guard 140 may be made of a flexible material, which in one non-limiting exemplary embodiment is heat resistant silicone. In other embodiments, only the bellows portion may be made of a flexible material, and the protective portion 195 may be made from the same or similar rigid material as the helmet shell 105.

As will be appreciated, it can be advantageous to form the neck guard 140 of a flexible material to provide increased comfort and flexibility to the user during the normal movements expected in use. For example, a user may need to rotate or shift their head during a welding operation, and a flexible neck guard 140 (flexing at the bellows portion 190) may allow this movement with less resistance and more comfort than a rigid neck guard permits. This can save time by reducing the need for the user to pause during a welding operation to adjust their helmet position, enabling the user to continuously weld while being able to freely rotate, tilt, and/or shift their head accordingly.

Figure 3:
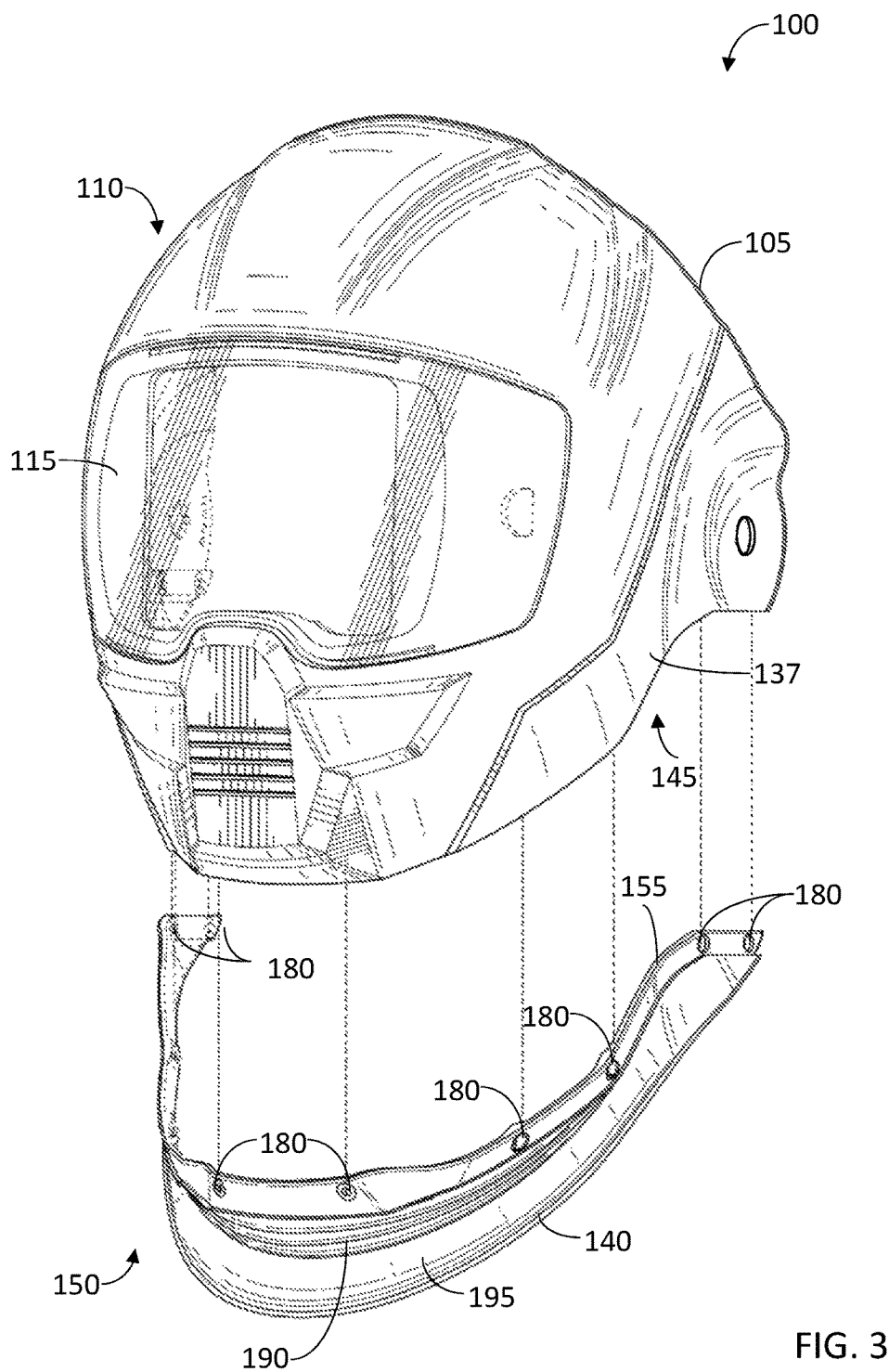
FIG. 3 is a front perspective view illustrating an embodiment of the welding helmet of FIG. 1, with the neck guard in a detached configuration.

As previously mentioned, the neck guard 140 may be removably attachable to the helmet shell 105. FIGS. 1 and 2 illustrate the neck guard 140 attached to the helmet shell 105, and FIGS. 3 and 4 illustrate the neck guard 140 detached from the helmet shell 105. In the illustrated embodiment the neck guard 140 is attachable to a bottom portion 145 of the helmet shell 105. As best seen in FIGS. 3 and 4, the neck guard 140 may include a lip 155 at an upper edge portion 160 of the neck guard 140 that follows the neck guard contour 150. The upper edge portion 160 may be positioned and configured to mate with the bottom portion 145 of the helmet shell 105 via the lip 155.

As more clearly shown in FIGS. 2 and 4, the neck guard 140 may be attachable to the interior surface 135 of the helmet shell 105 along the bottom portion 145 of the shell. A bottom edge 165 of the bottom portion 145 of the helmet shell 105 may abut or otherwise engage the lip 155 of the neck guard 150 so that the lip 155 overlaps a lower portion 170 of the interior surface 135 of the helmet shell 105, as shown in FIG. 2. This overlapping arrangement permits easy alignment of the neck guard 150 with the helmet shell. As can be seen, the neck guard 150 may have a predetermined shape or contour that is configured to correspond to the shape or contour of the bottom portion 145 of the helmet shell.

The neck guard 140 may be removably attachable to the helmet shell 105 by a plurality of fasteners 175. In one non-limiting exemplary embodiment, the fasteners 175 are screws. The neck guard 140 may have a plurality of apertures 180 for receiving respective fasteners 175 therethrough. The interior surface 135 of the helmet shell 105 may include a plurality of holes 185, disposed along the lower portion 170 of the interior surface 135 of the helmet shell 105. The neck guard 140 may be aligned along the bottom portion 145 of the helmet shell 105, so that the neck guard contour 150 and at least a portion of the helmet shell contour 110 are aligned, with the lip 155 of the neck guard 140 overlapping the lower portion 170 of the interior surface 135 of the helmet shell 105. The respective fasteners 175 may extend through the respective plurality of apertures 180 of the neck guard 140 and into the respective plurality of holes 185 of the helmet shell 105, thereby attaching the neck guard 140 to the helmet shell 105. In an embodiment, the plurality of holes 185 are blind holes, so the fasteners 175 are inserted from the interior surface 135 of the helmet shell 105, as shown in the rear perspective views of FIGS. 2 and 4. Blind holes in the helmet shell 105 may be advantageous to maintain an aesthetically pleasing look of the helmet shell 105. For example, in the illustrated embodiment the fasteners 175 are not visible on an exterior surface 137 of the helmet shell 105.

Although fasteners 175 are described for coupling the neck guard 140 and the helmet shell 105 through respective apertures 180 and holes 185, it should be understood that the neck guard 140 may be removably attachable to the helmet shell 105 by any appropriate coupling arrangement, including but not limited to clips, clamps, slides, switches, pins, buttons, Velcro®, magnets, adhesives and the like. Additionally, while a plurality of fasteners 175, apertures 180, and holes 185 are described, it should also be understood that the neck guard 140 may be removably attachable to the helmet shell 105 at a single attachment point.

Figure 7:
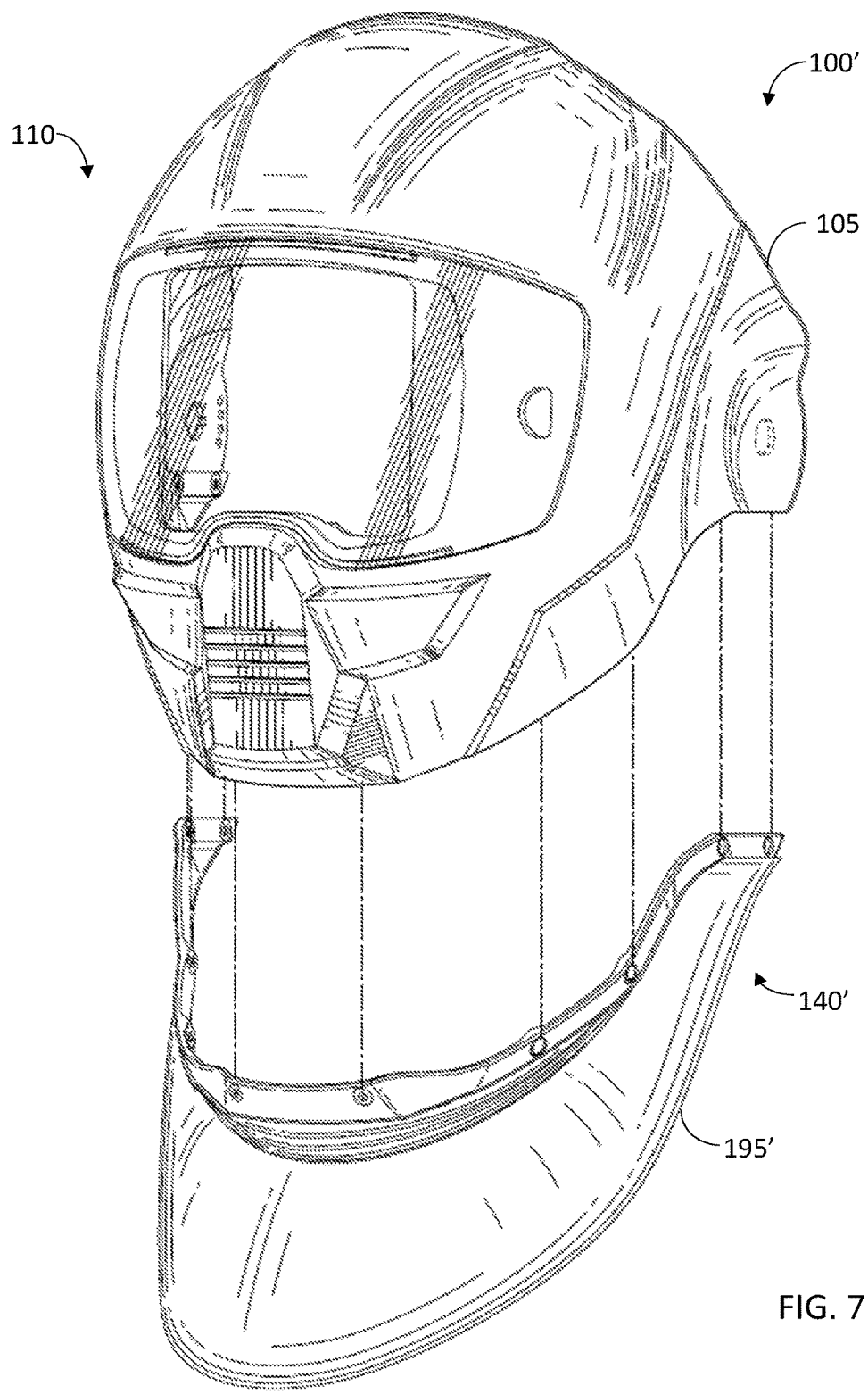
FIG. 7 is a front perspective view illustrating an embodiment of the welding helmet and a detached neck guard in accordance with the present disclosure.

As will be appreciated, it is advantageous for a user to have a removably attachable neck guard 140 and helmet shell 105, for example, to replace the neck guard 140 without having to replace the welding helmet 100. For example, the neck guard 140 may wear faster than the helmet shell 105 when the neck guard and helmet shells are provided as different materials. The removably attachable neck guard 140 also may allow for the user to have one or more neck guards 140 as spare parts for the welding helmet 100. For example, the user may desire to have one neck guard 140 formed of a rigid material, and a second neck guard 140 formed of a flexible material, and may interchange them with a single helmet shell 105 depending on the welding operation and requirements. Additionally, the neck guard 140 may be provided in a variety of different sizes. For example, the user may need or desire greater or less protection coverage depending on the welding operation. FIG. 7 illustrates a neck guard 140' having a protective portion 195' that is substantially larger than the protective portion 195 of FIGS. 1-6. Such a larger protective portion 195' may be appropriate for heavy duty welding operations in which the user needs or desires increased protective coverage, including but not limited to at least a portion of the user's neck and chest. By contrast, for lighter welding operations the user may only desire coverage of a portion of their neck. It is also contemplated that for some welding, grinding or other operations the user may remove the neck guard 140 entirely from the helmet shell 105.

As described above, the neck guard 140, 140' may be removably attachable to the helmet shell 105, and may be sized, or provided in different materials, to accommodate different welding operations and/or user preferences. This customization of the neck guard 140, 140' with the helmet shell 105 advantageously allows the user to select the appropriate neck guard 140, 140' without having to change to a different welding helmet 100. The modular configuration of the welding helmet 100, 100' saves time for the user in only switching neck guards 140, 140' as desired, as the user's welding preferences may be pre-programmed and/or pre-set in the welding helmet to a particular user, such as auto-darkening preferences of the auto-darkening screen 130, and/or head gear adjustments.

As shown more clearly in FIGS. 1, 3, and 7, a protective portion 195, 195' of the neck guard 140, 140' may provide a protective cover over at least a portion of any of a user's head, neck, and chest. The protective portion 195, 195' may be curved to accommodate the user when the welding helmet 100 is fitted to the head of the user, e.g., around at least a portion of the user's neck below his chin. FIG. 7 illustrates an extended protective portion 195', to provide additional protection of a user during a welding operation. As mentioned, some welding operations may generate higher amounts of weld spatter and/or debris over a larger workspace, and thus it can be advantageous to provide the extended protective portion 195' to protect a user during such welding operations. As described above, the neck guard 140', including the bellows portion 190' and the extended protective portion 195', may be formed of a heat resistant, flexible material, e.g., silicone.

In some embodiments a kit can be provided in which a plurality of different removable neck guards are included to allow a user to select an appropriate neck guard from the kit to use for a particular welding operation. Each of the neck guards 140, 140' in the kit may be configured to attach to the same welding helmet shell 105 so that the user can select and interchange different neck guards depending on user preference and/or the welding operation to be performed. In some embodiments the different neck guards 140, 140' may be made from different materials, may have different sized protective portions 195, 195' and may be flexible or rigid. All of the different neck guards 140, 140' may have a predetermined contour that is configured to conform to, align with, and attach to, the same welding helmet shell.

As used herein, an element or operation recited in the singular and proceeded with the word "a" or "an" should be understood as not excluding plural elements or operations, unless such exclusion is explicitly recited. Furthermore, references to "one embodiment" of the present disclosure are not intended to be interpreted as excluding the existence of additional embodiments that also incorporate the recited features.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. A welding helmet comprising:
   a helmet shell contoured to substantially cover a user's face; and
   a neck guard removably attachable to a bottom portion of the helmet shell, the neck guard having a predetermined contour aligning with a portion of the helmet shell contour and configured to cover at least a portion of a user's neck when the welding helmet is fitted to the head of the user,
   wherein the neck guard includes:
   a lip configured to abut a bottom edge of the helmet shell to align the neck guard with the helmet shell;
   a flexible portion extending from the lip and including a plurality of surface elements configured to permit flexing of the neck guard in response to user movement;
   a protective portion extending from the flexible portion, wherein the protective portion does not include the plurality of surface elements configured to permit flexing of the neck guard.

2. The welding helmet according to claim 1, wherein the helmet shell and the protective portion of the neck guard are made of a first material, and the flexible portion is made of a second material different from the first material.

3. The welding helmet according to claim 1, wherein the neck guard is removably attachable to the helmet shell by a plurality of fasteners.

4. The welding helmet according to claim 1, wherein the neck guard is removably attachable to an interior surface of the helmet shell.

5. The welding helmet according to claim 4, wherein the interior surface of the helmet shell includes a plurality of holes for receiving a plurality of fasteners to removably attach the neck guard.

6. The welding helmet according to claim 5, wherein the plurality of holes on the interior surface of the helmet shell are blind holes.

7. The welding helmet according to claim 6, wherein the neck guard includes a plurality of apertures for receiving the plurality of fasteners.

8. The welding helmet according to claim 7, wherein the plurality of apertures on the neck guard are positioned to align with the plurality of blind holes on the interior surface of the helmet shell to align the neck guard contour with the helmet shell contour.

9. The welding helmet according to claim 2, wherein the second material of the flexible portion is more flexible than the first material of the protective portion of the neck guard.

10. The welding helmet according to claim 9, wherein the second material is a silicone material.

11. The welding helmet according to claim 9, wherein the surface elements configured to permit flexing of the neck guard are configured as bellows and are disposed parallel to the neck guard contour.

12. The welding helmet according to claim 9, wherein the surface elements configured to permit flexing of the neck guard are configured as bellows.

13. The welding helmet according to claim 1, wherein the protective portion of the neck guard is rigid.

14. The welding helmet according to claim 13, wherein the neck guard is made of a heat resistant plastic material.

15. The welding helmet according to claim 1, wherein the protective portion is configured to cover at least a portion of a user's neck.

16. The welding helmet according to claim 1, wherein the protective portion is configured to cover at least a portion of one of a user's head, neck, chest, shoulders, back, and arms.

17. The welding helmet according to claim 16, wherein the protective portion is made of a material to protect a user from weld spatter occurring during a welding application.

18. The welding helmet according to claim 17, wherein the protective portion is made of at least one of a synthetic material, rubber, or leather.

19. A welding helmet kit comprising:
a helmet shell contoured to substantially cover a user's face;
a flexible neck guard removably attachable to a bottom portion of the helmet shell; and
a rigid neck guard removably attachable to a bottom portion of the helmet shell;
wherein the flexible neck guard and the rigid neck guard have a predetermined contour aligning with the helmet shell contour and are configured to cover at least a portion of a user's neck when the welding helmet is fitted to the head of a user,
wherein the flexible neck guard includes:
a lip configured to abut a bottom edge of the helmet shell to align the flexible neck guard with the helmet shell;
a bellows portion extending from the lip and including a plurality of bellows elements configured to permit flexing of the neck guard in response to user movement;
a protective portion extending from the bellows portion, wherein the protective portion does not include the plurality of bellows elements.

20. The welding helmet kit according to claim 19, wherein at least one of the flexible and rigid neck guards is removably attachable to the helmet shell by a plurality of fasteners.

* * * * *